United States Patent [19]

Saville

[11] Patent Number: 4,736,083
[45] Date of Patent: * Apr. 5, 1988

[54] MICROWAVE HEATING DIGESTION VESSEL

[75] Inventor: Russell H. Saville, Minnetonka, Minn.

[73] Assignee: Savillex Corporation, Minnetonka, Minn.

[*] Notice: The portion of the term of this patent subsequent to Sep. 23, 2003 has been disclaimed.

[21] Appl. No.: 909,210

[22] Filed: Sep. 19, 1986

Related U.S. Application Data

[63] Continuation-in-part of Ser. No. 702,639, Feb. 19, 1985, Pat. No. 4,613,738.

[51] Int. Cl.$^4$ .................................................. H05B 6/80
[52] U.S. Cl. ........................ 219/10.55 R; 219/10.55 E; 220/316; 215/312; 215/315
[58] Field of Search .............. 219/10.55 R, 10.55 E, 219/431, 440; 220/366, 367, 371, 372, 316; 215/312, 315, 314, 311; 99/369, DIG. 14; 426/241, 243, 403

[56] References Cited

U.S. PATENT DOCUMENTS

| | | | |
|---|---|---|---|
| 1,973,258 | 9/1934 | Jensen | 220/372 X |
| 2,198,125 | 4/1940 | Nelson | 220/366 |
| 2,226,593 | 12/1940 | Stroupe et al. | 220/316 |
| 2,860,811 | 11/1958 | Hessler | 220/372 X |
| 3,155,292 | 11/1964 | Webster | 220/367 X |
| 4,000,829 | 1/1977 | Johnson, Jr. et al. | 220/367 X |
| 4,343,325 | 8/1982 | Fallon | 220/316 X |
| 4,406,861 | 9/1983 | Beauvais et al. | 219/10.55 R X |
| 4,490,597 | 12/1984 | Mengel | 219/10.55 E |
| 4,613,738 | 9/1986 | Saville | 219/10.55 R |

Primary Examiner—Philip H. Leung
Attorney, Agent, or Firm—Hugh D. Jaeger

[57] ABSTRACT

Microwave digestion vessel of Teflon PFA material including a Teflon PFA vessel with a threaded top and a Teflon PFA cap with internal threads for engaging the vessel threads. A valve assembly extends upwardly from a center portion of the cap and includes a valve seat, a valve ball internal thereto, a Teflon spring uniquely configured and a valve cap holding the spring and ball into the ball seat of the valve seat. An exhaust hole is provided out one side of the valve cap. The vessel includes a flange for encompassing a lower portion of the cap for pressure expansion protection. A ring with an adjoining flange is also provided for the cap to provide for pressure expansion protection. An alternative embodiment is illustrated with a side venting orifice with filtering, a dialed in spring pressure, and a spring cavity with an integral valving surface.

10 Claims, 8 Drawing Sheets

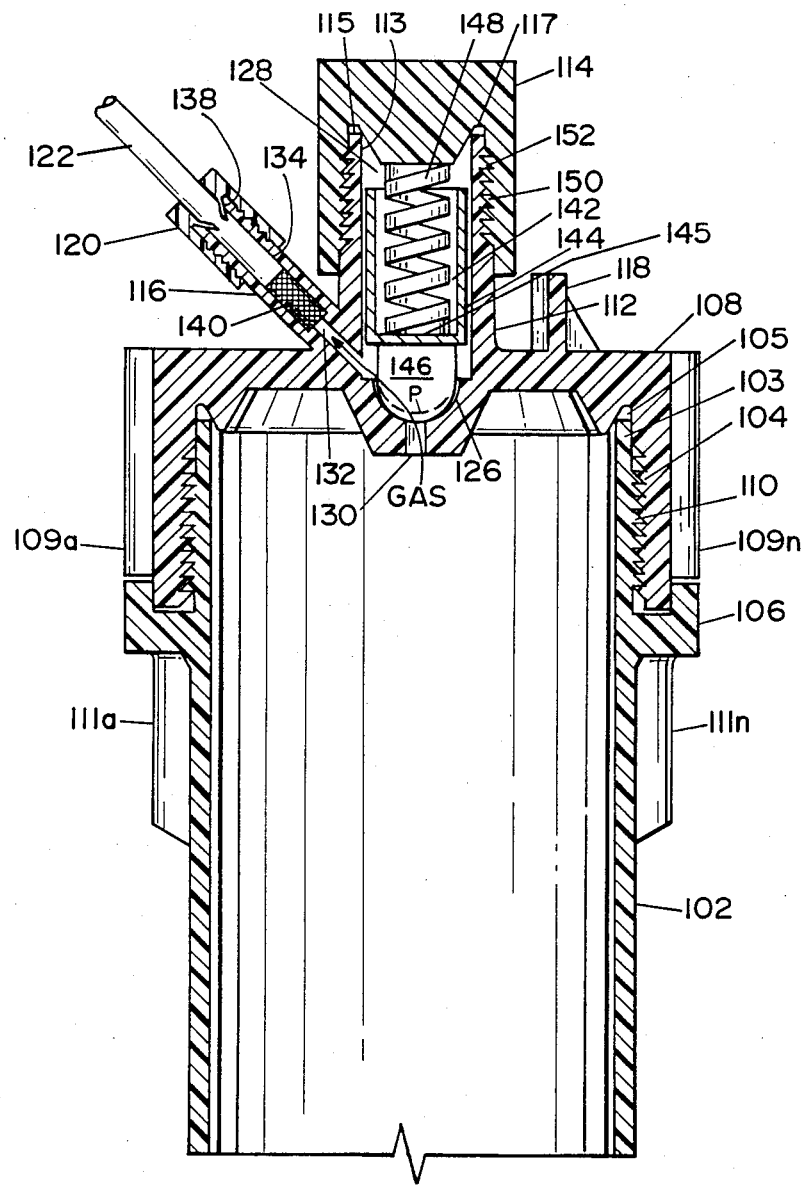

MICROWAVE HEATING DIGESTION VESSEL

CROSS REFERENCES TO CO-PENDING APPLICATIONS

The patent application is a continuation-in-part of Ser. No. 702,639, filed Feb. 19, 1985, now U.S. Pat. No. 4,613,738, entitled "Microwave Digestion Vessel".

BACKGROUND OF THE INVENTION

1. Field of the Invention

The present invention pertains to a digestion vessel, and more particularly, pertains to a microwave digestion vessel for use in a microwave oven with a valve assembly for venting high pressure, the valve including the use of a spring such as a Teflon spring acting against a ball such as a Teflon ball.

2. Description of the Prior Art

Before the advent of microwave heating and microwave ovens, considerable time was required to dissolve samples for chemical analysis. This was especially so for elemental trace analysis, such as in the oil industry, the mining industry, and other related areas, including medical laboratories. Digestions were performed in open vessels on hot plates, or other heating devices, resulting in long and extended digestion times, in addition to the exposure of personnel to caustic and harmful exhaust fumes from boiling acids or other digestion subjects.

With the advent of microwave heating and microwave ovens, elemental trace analysis became ever more so common, especially in utilizing microwave digestion vessels in element trace analysis and the chemical procedures. The prior art problem with the using of digestion vessels was that there was a certain amount of guess work required in the microwave heating techniques, especially pertaining to temperature, pressure, and time for a digestion procedure. During microwave heating it was possible, at elevated temperatures, to cause digestion vessels to expand considerably beyond normal size.

With the advent of Teflon PFA molded vessels, the Teflon PFA material provided a microwave digestion vessel which would function at elevated pressures and temperatures over time. Irrespective, there was still the necessity in the art for providing for the venting of high pressures and collection of vapors or gases in a slow controlled manner during microwave digestions.

Early attempts provided digestion vessels with valving assemblies with springs of ferrous or non ferrous alloys in a valving arrangement, but this proved to be difficult as such a metallic assembly in a microwave oven cavity may cause arcing between adjacent metallic members, and required special shielding and time consuming periodic cleaning off of surface oxidation for proper non-impeded spring operation. These springs would also react with digestion vapors and gases offering potential contamination of the digestion container and contents thereof. These springs also deteriorated due to chemical reactions with digestion vapors, thus breaking down the spring qualities causing the springs to fail or relieve at a pressure other than desired allowing vessel vapors and contents to be expelled overboard at an inopportune time.

The present invention overcomes the disadvantages of the prior art by providing a microwave digestion vessel including a valve assembly, utilizing a Teflon ball and Teflon non-corrosive, non-contaminating spring, and including a pressure release hole out the side of the valve for exhausting pressure on actuation of the valve spring in a slow controlled manner.

SUMMARY OF THE INVENTION

The general purpose of the present invention is a microwave digestion vessel for use in digestion procedures in a microwave oven. Particularly, the Teflon PFA digestion vessel includes a Teflon valve assembly, the Teflon valve assembly including a unique Teflon spring acting in conjunction with a Teflon ball for venting of high pressures in a slow controlled manner.

According to one embodiment of the present invention, there is provided a microwave digestion vessel including a Teflon PFA vessel with a threaded top, a Teflon PFA cap with mating threads to the vessel, the cap including a valve assembly having a valve seat, the valve seat including a ball seat and a Teflon non-corrosive, non-contaminating valve spring acting between a valve cap, which threads onto the valve seat, and a Teflon ball. An exhaust hole is provided in one side of the valve seat for exhausting gases under pressure. The Teflon valve spring includes a section of spring with two open cylinders on each end. A plurality of spacing nipples extend outwardly from the sides of the cylinders, as well as the sections of spring, for spacing the spring within the round interior section leading to the valve seat. A small clearance is provided adjacent to the ball at the valve seat for slow controlled venting of pressure.

According to another embodiment of the present invention, there is provided a digestion vessel with a enclosed spring cavity having an integral ball seat, and a side venting orifice adjacent to a lower orifice for short path flow and venting of gases.

One significant aspect and feature of the present invention is a Teflon PFA microwave digestion vessel with a Teflon venting valve including a Teflon spring for relieving high pressures during digestion procedures. Other like materials can also be utilized.

Another significant aspect and feature of the present invention is a Teflon PFA microwave digestion vessel utilizing a Teflon valve spring in a Teflon valve assembly. The Teflon valve spring is transparent to microwave energy, and does not heat up during the microwave heating process in the microwave oven, as well as being non-contaminating and non-corrosive.

A further significant aspect and feature of the present invention is dialing in a spring pressure exerted by a ball against the valve seat.

Anther significant aspect and feature of the present invention is a Teflon valve spring enclosed in a sleeve shielding and protecting the spring from contaminating exhaust vapors.

An additional significant aspect and feature of the present invention is a hydrophobic filter in the outlet port of the relief valve.

Having thus described the embodiments of the present invention, it is a principal object hereof to provide a microwave digestion vessel with a pressure relieving valve for use in a microwave oven during digestion procedures for bleeding off pressure and fumes in a controlled manner.

One object of the present invention is to provide a microwave digestion vessel which includes an entire Teflon valve assembly for relieving high pressure build-up in the vessel during digestion procedures in a microwave oven utilizing a slow controlled venting procedure based on the design of the valve.

Another object of the present invention is to provide a microwave digestion vessel which includes a non-corrosive Teflon spring which will not corrode and impede valve operation.

An additional object of the present invention is to provide a microwave digestion vessel which includes a non-corrosive Teflon spring which will not contaminate the gases or vapors from the vessel nor the contents thereof.

A further object of the present invention is a short path of flow of gases to exit from the digestion vessel to the atmosphere. In the unlikely event of spring failure, gases will inherently vent through the orifices, preventing rupture or explosion of the vessel.

Yet a further object of the present invention is to provide a protected spring enclosure preventing and minimizing contact between the spring and corrosive hot vessel vapors.

A further object of the present invention is to provide a safe microwave digestion vessel which will not pressurize if spring failure occurs.

Another object of the present invention is to provide a hydrophobic filter in the output of the vale in the microwave digestion vessel which will pass only gases and contain liquids within.

BRIEF DESCRIPTION OF THE DRAWINGS

FIG. 10 illustrates a cross-section side view of FIG. 7 taken along line 9—9 of FIG. 7; and FIG. 11 illustrates an alternate embodiment of an alternative structure of a hydrophobic vent insert.

DESCRIPTION OF THE PREFERRED EMBODIMENTS

Figure 1:
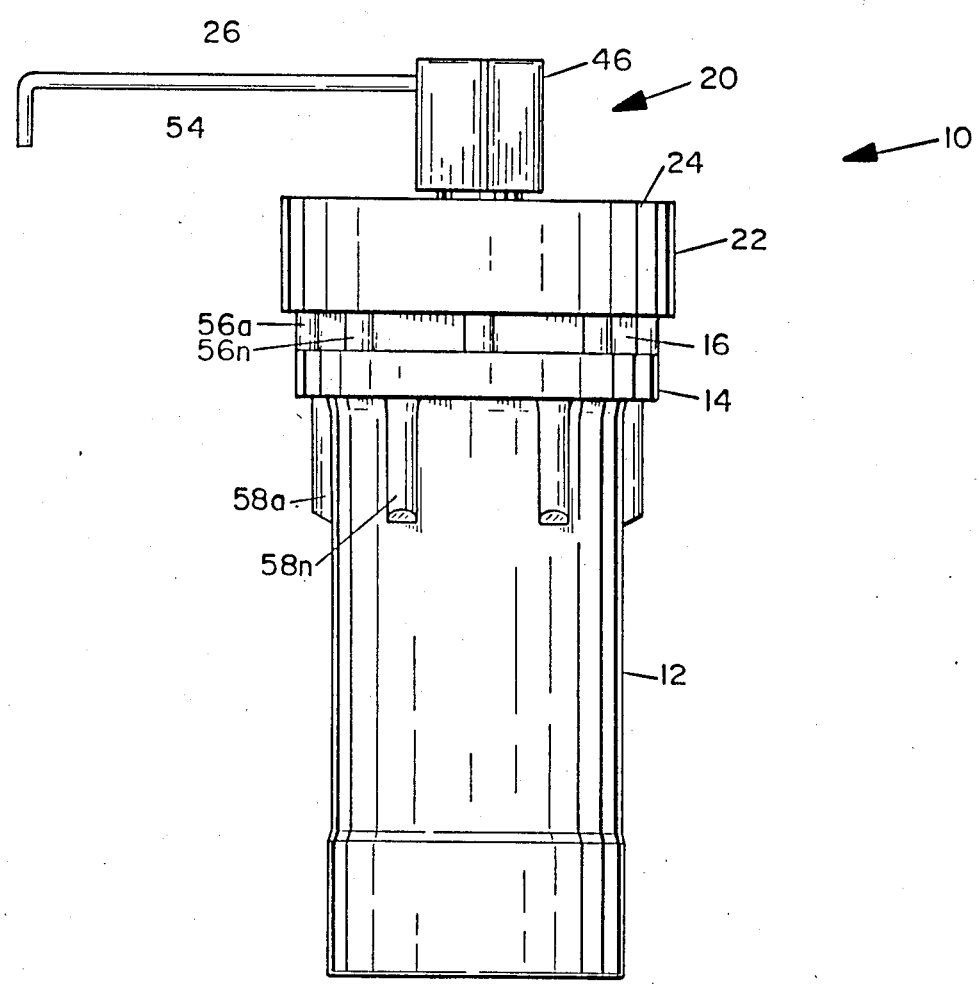
FIG. 1 illustrates a side view of a microwave digestion vessel including a pressure relieving valve assembly.
Figure 2:
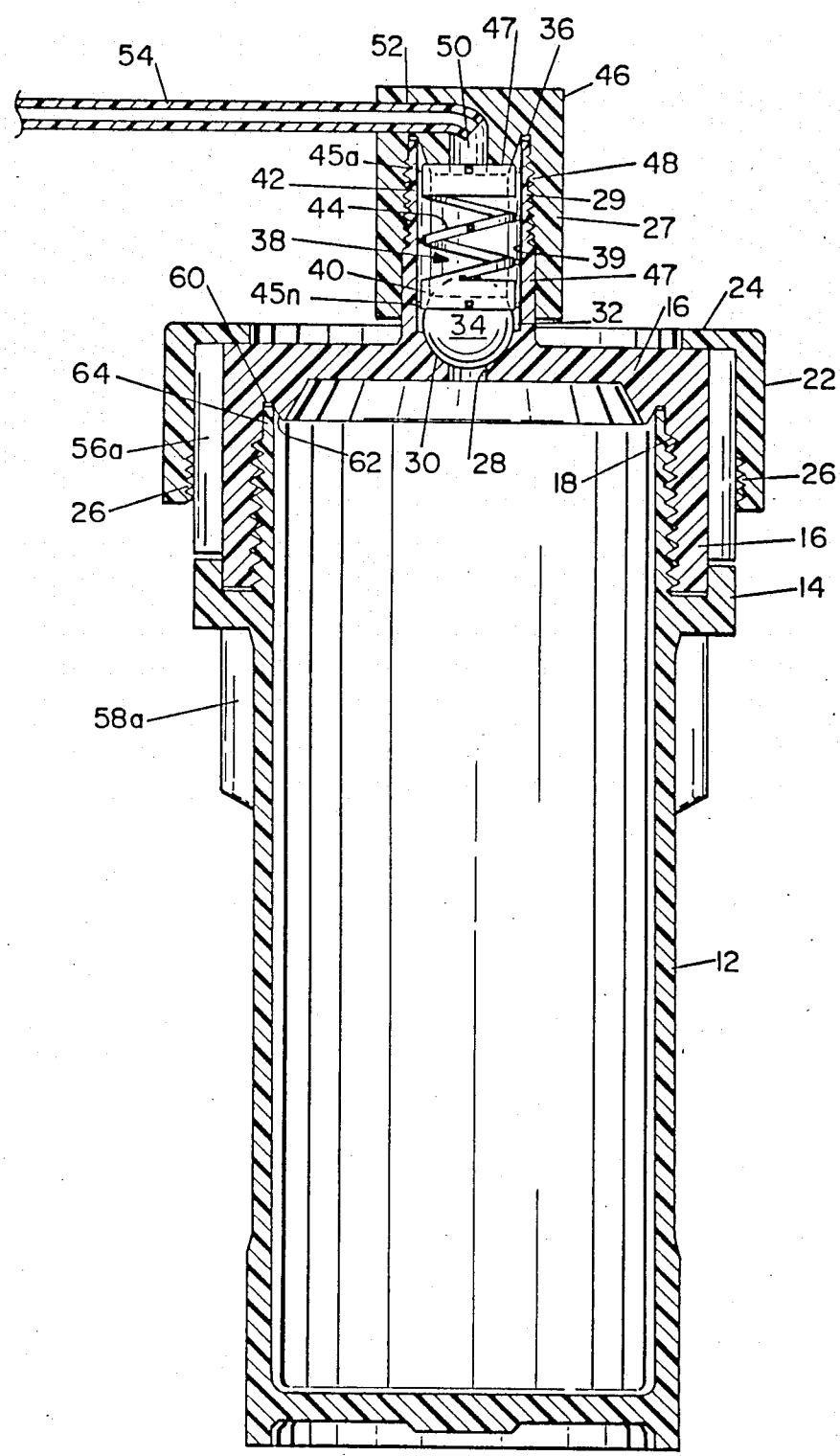
FIG. 2 illustrates a cross-section of the vessel and valve assembly.

FIG. 1 illustrates a side view of a microwave digestion vessel 10 including a Teflon PFA vessel 12 with a threaded top 13, as illustrated in FIG. 2, and a molding flange 14 for encompassing a lower portion of a Teflon PFA cap 16 with internal threads 18, as illustrated in FIG. 2. A valve body 20 extends upwardly from the top of the cap 16, and is described in detail in FIG. 2. A venting tube 54 extends outwardly from the valve cap 46 as later described. A retaining ring 22 with a top leading edge 24 surrounds an upper portion of the cap 16 and includes internal threads 26 as illustrated in FIG. 2. The ring 22 provides that cap 16 cannot expand away from the vessel 12 during microwave digestion procedures at elevated temperatures. Threads 26 are self threading providing for loose screwing of the ring 22 on and off of the cap 16 as required.

FIG. 2 illustrates a cross-sectional view of FIG. 1 where all numerals correspond to those elements previously described. Particularly, the valve body 20 includes a central hole 28, a ball seat 30, and narrow aperture clearance 32 upwardly extending on an interior section of an upwardly extending valve body wall 27. The ball seat is positioned about a lower portion of a ball 34 in the top wall of the cap 16. Top 36 of the valve body 20 is planar providing for a positive stop. The Teflon ball 34 engages against the ball seat 30. A Teflon spiral spring 38 engages within the internal cylindrical wall section 39 of the valve body 20. The Teflon spring 38 includes two open cylindrical members 40 and 42 connected by a section of spiral spring 44. A plurality of spacing nipples 45a–45n extend outwardly from the members 40–44. Each cylindrical member 40 and 42 includes a 45' chamber or a rounded chamber, and a flat surface as later described in FIG. 3. A valve cap 46 includes interior threads 48 which engage with threads 29 of the valve body 47, providing for an integral fit. A top underside surface 47 of valve cap 46 is also planar providing for a positive stop and mating with the planar surface 36 of valve body 20. A hole 50 extends upwardly to a side hole 52 for venting of pressures out the side of the valve cap 46. A relief tube 54 can be pressed into the side hole 50 for relieving and draining residual fluids into a second container as later described. The Teflon spring can be glass filled, a composite, or the like, for maintaining a proper flexible spring coefficient. The vessel bottom, vessel cap, and valve seat and cap, as well as the ball and spring can also be made out of other materials than Teflon PFA. The spring section can also assume any other like geometrical configuration such as a "Z" shape, etc., rather than the spiral shape as illustrated. The ring 22 can be of a polymer, a composite, or other like material. The flange 14 is of an annular right angle shape so that the lower portion of the cap 16 screws and extends down into the area created by the encompassing annular flange so that the cap 16 will not expand off of the threaded vessel top 13 during digestion processes which create height pressures. The top of the vessel 12 includes a flat planar lip edge 60 with annular exterior edge 64. The interior of the cap 12 includes an angled annular interior wedge edge 62. As the cap 16 is screwed on tightly, angled wedge edge 62 exerts outward force upon lip edge 60 and forces it and the annular exterior edge 64 outwardly affecting a secure pressurized seal between edge 64 and the adjacent interior cap surface, as well as between wedge edge 62 and portions of lip edge 60. It is illustrated that the two planar surfaces 36 and 47 of valve body 20 and valve cap 46, respectively, mate flush with each other's surfaces.

Figure 3:
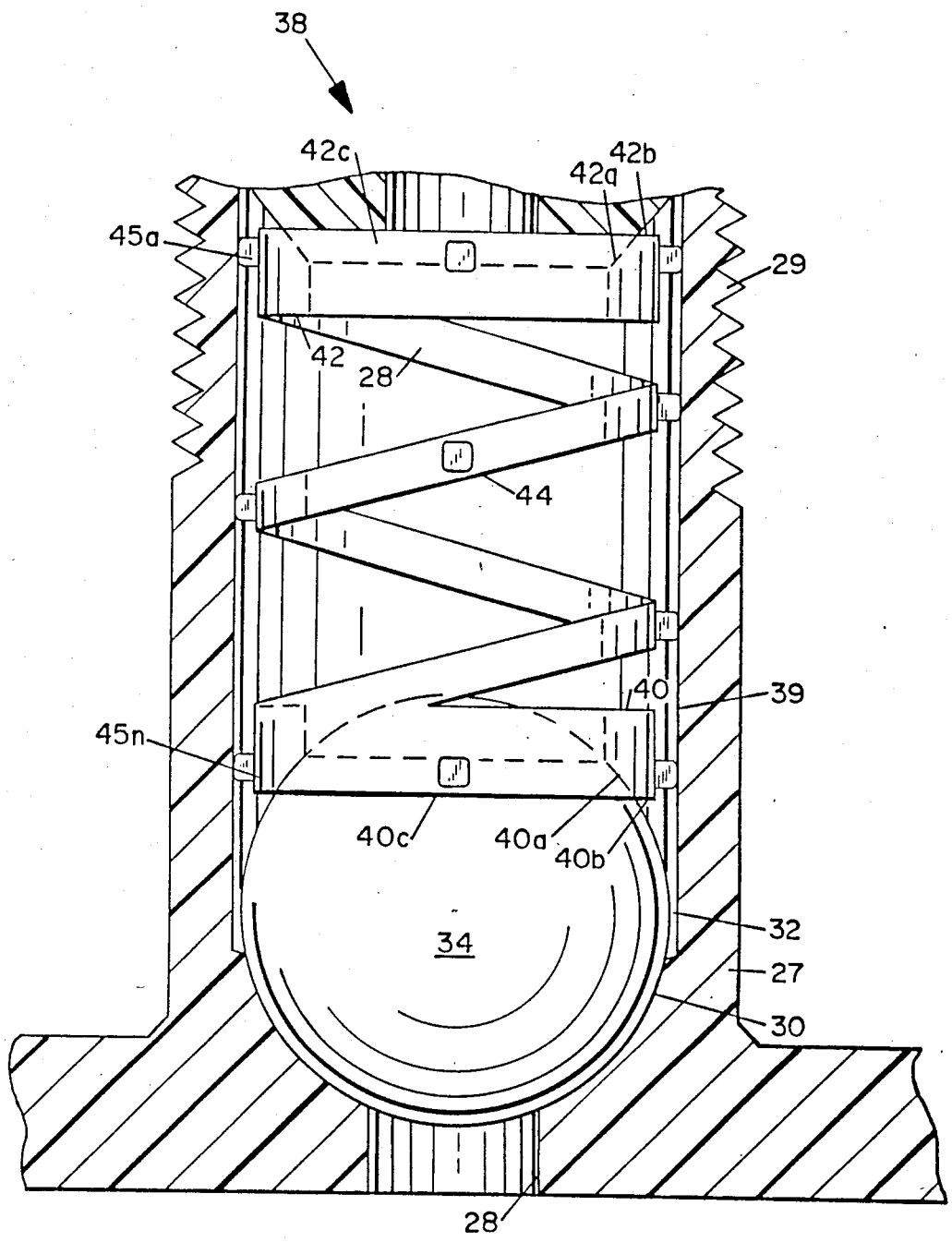
FIG. 3 illustrates an enlarged view of a portion of the valve assembly.

FIG. 3 illustrates an enlarged view of the valve body 27, ball 34, and the spring 38. Each open cylindrical member 40 and 42, includes a 45' or conforming chamber 40a and 42a and a flat surface 40b and 42b. Hollow portions 40c and 42c through members 40 and 42 are provided for venting of gases, vapors, etc. The spring 38 is interchangeable in either direction for ease of installation. The spring includes a plurality of spacing nipples 45a–45n for spacing elements 40–44 from the side wall 39. The spring can be of one to ten turns, while two turns are illustrated by way of example and for purposes of illustration only. The transition from the ball seat 30 to the clearance of each side of the 34 in hole 28 is in the range of 20/1000 inch for controlling pressure release, although any other suitable dimension can be utilized as parameters would require.

Figure 4:
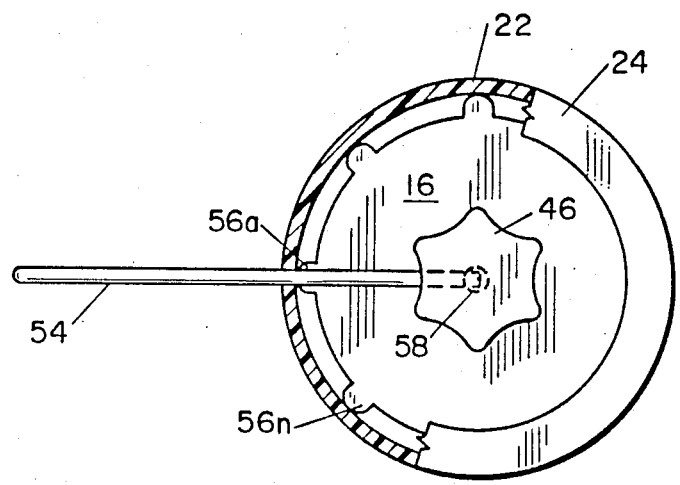
FIG. 4 illustrates a partial cutaway top view of the vessel.

FIG. 4 illustrates a top view in partial cross section of the present invention where all numerals correspond to those elements previously described. In this view, as well as the bottom view of FIG. 5, a plurality of downwardly extending lugs 56a-56n are provided for the cap 16, and a plurality of like downwardly extending lugs 58a-58n are provided for the the vessel 12. These ribs provide point contact gripping point for a lug tool to separate the top and bottom of the vessel. The lower lugs 58a-58n are molded into the lower edge of flange 14 for structural integrity and stability.

Figure 5:
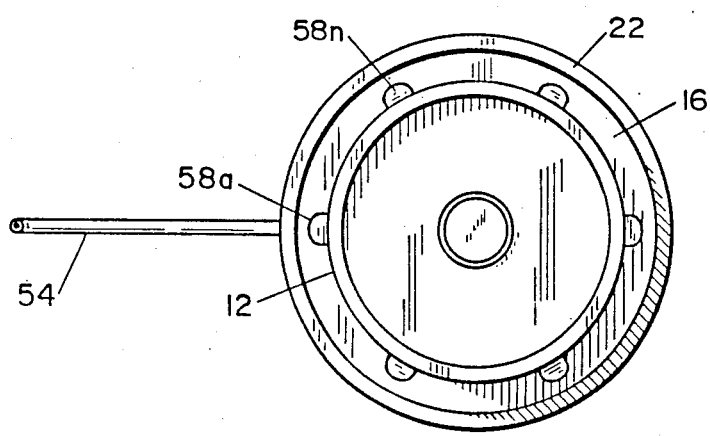
FIG. 5 illustrates a bottom view of the vessel.

FIG. 5 illustrates a bottom view of the vessel where all numbers correspond to those elements previously described.

MODE OF OPERATION

Figure 6:
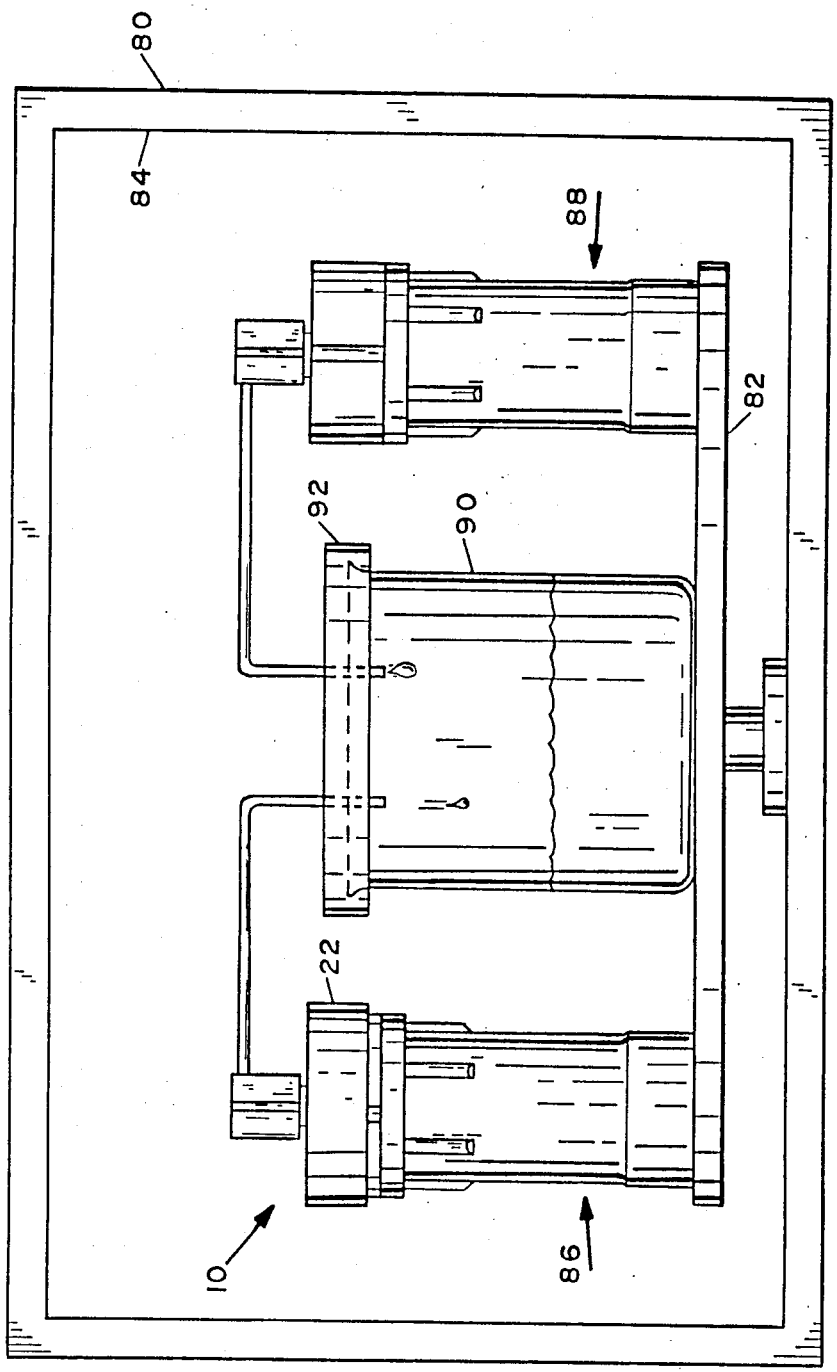
FIG. 6 illustrates vessels used in a microwave oven during a microwave digestion procedure.

FIG. 6 illustrates the mode of operation of the present invention, illustrating a microwave oven 80, and a turntable 82 in the microwave oven cavity 84 for supporting a plurality of digestion vessels 10 about the perimeter of the turntable 82. Two digestion vessels 86 and 88 are shown by way of example and for purposes of illustration only. A container 90 positions on the axis of the turntable. The microwave digestion vessels include relief tubes from the hole of each valve assembly coupled into the container for discharge of any residual pressure, vapors, or liquids, etc. The container 90 can include a cap 92. The container and cap can be made of Teflon, glass, or any other material transparent to microwave energy.

In operation, and referring particularly to FIGS. 2 and 3, when the pressure becomes high enough to overcome the spring coefficient, the ball 34 is unseated off the ball seat 30, and pressure flows around the circumference of the ball at clearance 32, up and around the open cylinders 40 and 42 including the spring section 44 as spaced by the spacing nipples 40a-40n. Gas exhausts through the top surface of the cylinder 42 and out through the vent holes 50 and 52 and tube 54. The tube 54 channels the gas and vapors into the container 90 as illustrated in FIG. 5 or the unit can be operated with a short tube exhausting to open air inside the oven or with no tube. Each vessel can be used without the retaining ring 22 as so desired. The bottle, cap, and ring will be made of materials transparent to microwave energy. The material, while indicated as a fluoropolymer, such as Teflon PFA, can include a glass fiber filler, rag content, or a composite material. The ring can also be made of a polymer as required. The vessels can be used with or without the ring as illustrated in FIG. 5 where one vessel is illustrated with the ring 22 and the other vessel is without the ring.

DESCRIPTION OF THE FIRST ALTERNATIVE EMBODIMENT

Figure 7:
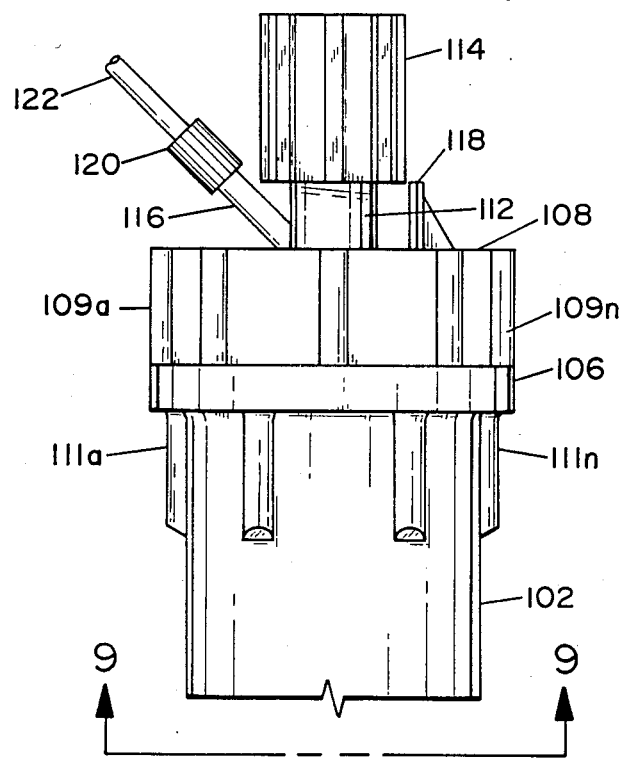
FIG. 7 illustrates a first alternative embodiment side view of a microwave digestion vessel including pressure relief valve.
Figure 9:
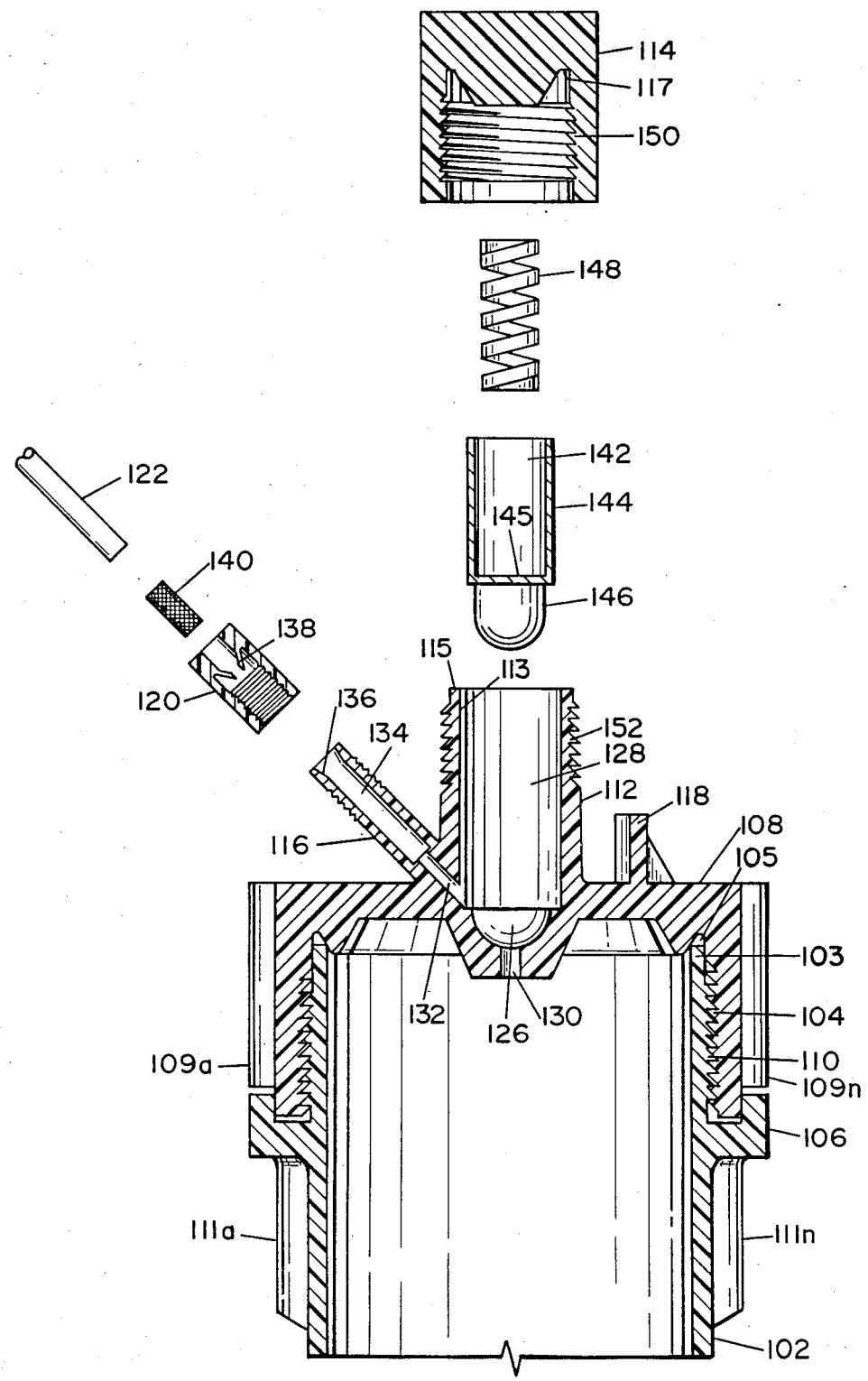
FIG. 9 illustrates an exploded view in cross section of an alternate embodiment.

FIG. 7 illustrates a side view of a first alternate embodiment of a microwave digestion vessel 100 including a vessel 102 of Teflon PFA or like material with a buttress threaded upper member 104 as illustrated in FIG. 9. A molded flange 106 encompasses a lower portion of a Teflon PFA vessel cap 108 including internal buttress threads 110 as illustrated in FIG. 9, although the molded flange 106 is not required for operation in low pressure functions. A threaded cap neck 112 extends from the upper surface of the cap 108. Cap 114 fits over and about neck 112. A configured, angled, threaded filter body member 116 intersects with the neck 112 and the top surface of the cap or lid 108. A pointer member 118 positions on the upper surface of cap 108 for determining and referencing preset adjustment of the relief internal valve as described in detail in FIGS. 9 and 10. Lugs 109a-109n and 111a-111n, as described in previous Figures position about and on cap 108 and vessel 102 for tightening of the cap 108 to the vessel 102. A knurled nut 120 with internal ferrels positions over and about the angled filter tube body 116 for securing a relief tube 122 to the filter body 116.

Figure 8:
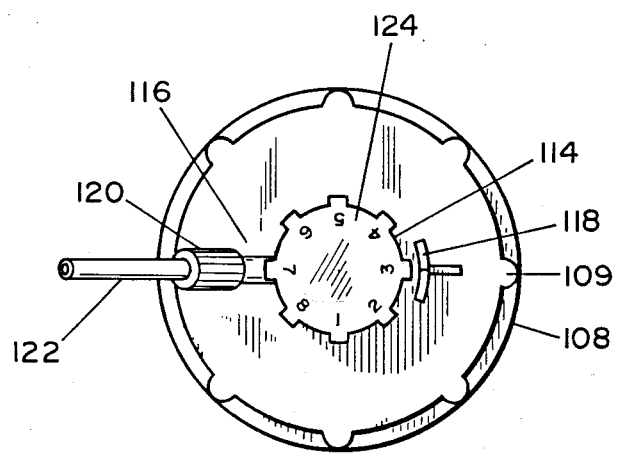
FIG. 8 illustrates a top view of alternate embodiment 7.

FIG. 8 illustrates a top view of the cap or lid 108 including the smaller cap 114, the adjustment reference numbers 124, the pointer 118 for referencing adjustment numbers 124, the filter body 116, the knurled nut 120 and the relief tube 122.

FIG. 9 illustrates an exploded view of the relief valve and outlet port of FIG. 7. The inner cylindrical portion 113 of threaded neck 112 and a semi-spherical cavity ball seat surface 126 in a lower portion of cap 108 form a valve cavity body 128. A small orifice 130 positions at the bottom of the valve cavity 128 to vent pressure from the interior of vessel 102 out through filter body tube 116 as described in later detail. A hole 132 positions between the vent cavity 128 and a larger hole 134 in the filter body 116 as illustrated. Beveled edge 136 at the outer portion of larger hole 134 accomodates a built-in integral ferrel surface 138 for positioning and securing a relief tube 122 to the filter body 116. A hydrophobic filter 140 at the end of relief tube 122 positions in the inner portion of larger hole 134 to relieve gas pressures and exclude liquids from exiting overboard. A spring cavity 142 is formed by walls of cylindrical sleeve 144. A solid radiused end 146 integral to the sleeve 144 positions at the end of the sleeve 144 and acts to serve as a valve when placed into cavity 128 and against valve hole 130. A spring 148 consisting of non-corrosive material such as being a spring coated with Teflon, a polymer material, a glass spring, a Teflon spring, or the like, positions in spring cavity 142 of the hollow sleeve 144. A threaded configured cap 114 similar to those in previous figures positions over and about the threaded neck 112. The top of threaded neck 112 forms an annular seal 115 to mate with the annular grove 117 in the inner top of cap 114. The spring 148 in the hollow sleeve 144 exerts downward pressure against flat surface 145 to radiused ball valve 146, thereby affecting a pressure seal of the radiused ball valve 146 in semispherical cavity 126 surface and sealing against the orifice 130. Fine interior buttressed threads 150 mate to fine exterior buttressed threads 152 of the neck 112 providing for vernier like fine adjustment of tension on spring 148, thereby allowing for fine tuning of the pressure relief differential as vessel pressures relieve through orifice 130, against valve ball 146, through hydroscopic filter 140 in filter body 116, and overboard through relief tube 122. The top of vessel 102 forms an annular ring 103 and effects a seal in annular groove 105 in cap 108 as illustrated.

FIG. 10 illustrates a cross-sectional assembled view of FIG. 9 where all numerals correspond to those elements previously described. Physical dimensions by way of example and not to be construed as limiting of the present invention include a 3/16" radius for the semi-spherical ball seat 126, a ⅜" wide spring 148, a 3/64" sleeve 144 thickness, a ¾" diameter cap 114, a 3/32" to ⅛" orifice 130, a ⅛" diameter orifice 132, 3/16"

O.D.×⅛" I.D. tubing 122, and a threaded diameter 0.600" buttress threaded GTPI 150 and 152.

FIG. 11 illustrates an alternative embodiment of structure for a hydrophobic vent insert 200. A hydrophobic vent insert 200 can in its entirety be placed within hole 134 in filter body 116 in lieu of hydrophobic filter 140. Configured male portion 202 mates into configured female portion 204 as illustrated. A small wafer like hydrophobic filter 206 is placed internally as illustrated, and gases flow between orifices 210 and 208, through the hydrophobic insert 200, and overboard through vent tube 122.

MODE OF OPERATION

During digestion in the vessel, the gas vents out during predigestion, allowing excess gas to escape without loosing any liquids inside the container. The adjustable nut allows for dialing in any predetermined pressure for different digestion procedures. A user can also open the adjustment nut before removing the main cap, allowing for the exhausting of any built-up pressure through the vent. The spring can be reused, or in the event that the spring has experienced fatigue, the spring can also be exchanged. The thin sleeve protects the spring from hot gases during a digestion procedure, as the gases vent in a least distance path, and does not pass by the spring. In the unlikely event that there is a spring failure, the gases will inherently pass between the orifices and not allow for build-up and dangerous pressures within the digestion vessel. The area for the porous plug or permeable membrane allows for gases to vent as safely as possible. The permeable membrane could be as thin as 10 ml in any type of suitable microporous or filtering material. Of course, a two-piece assembly may also be utilized as illustrated in FIG. 11 for containing a thin disc or discs, such as for a hydrophobic vent. The springs can be made of any suitable materials, such as special alloys, Teflon coated, glass springs, glass-reinforced polymers, polymers or Teflon springs.

Various modifications can be made to the present invention as being within the scope and teachings of the disclosure. The hole 130 can be varied in diameter which would vary to release pressure at a desired level. Likewise, the spring compression is adjustable by the number of turns, diameter of the cross-section, etc., and any space between the top of the cap and the top of the sleeve 144 is adjustable. The sleeve 144 is a one-piece member. During digestion, the sleeve rises to allow gases to escape, but not liquids under digestion, as indicated by dashed line "P" in FIG. 10. An external filter could be used in lieu of the assemblies 140 and 200 of FIGS. 10 and 11. The spring can be of Teflon, a coated metal, ceramic, or any other suitable material. The disk or membrane is a porous material, and relieves the pressure differential accordingly.

I claim:

1. A moveable heating digestion vessel for use in a microwave oven during microwave heating digestion of a material, comprising:

a. a molded threaded fluorocarbon vessel and mating molded threaded fluorocarbon large cap for covering said vessel, said vessel and said large cap being transparent to microwave energy;

b. a valve body assembly portion of said large cap positioned on the top of said large cap and extending outwardly therefrom, said valve body assembly including a ball seat, a valve port extending from said ball seat inwardly through said large cap, a vent port opening extending from said ball seat outwardly through said large cap to the atmosphere, and an externally threaded hollow cylindrical neck coaxially aligned with said ball seat and extending outwardly from said large cap;

c. a valve ball member of fluorocarbon material, having a spherical end portion for mating with said ball seat and a hollow cylindrical portion for retention of spring assembly and limiting the range of travel of said ball member;

d. a threaded valve cap of fluorocarbon material for engaging on said threaded neck and having an interior stop for engagement with said cylindrical portion of said ball member to limit travel of said ball member;

e. indicia on said large cap and said threaded valve cap indicating the relative position; and, f. a non-metallic spring assembly positioned coaxially within said hollow cylindrical portion of said valve ball member and bearing against said threaded valve cap and said ball member to bias said ball member against said ball seat with a predetermined force, whereby said bias force and therefore also the internal pressure within said vessel required to open said valve ball member from said ball seat is adjustable by rotating said threaded valve cap on said valve body assembly and indicated by said indicia, and pressure is thereby relieved through said vent port opening.

2. The microwave heating digestion vessel of claim 1 wherein said molded threaded vessel, said valve cap and said large cap are made of fluorocarbons.

3. The microwave heating digestion vessel of claim 1 including an encompassing cylindrical flange extending upwardly from a mid portion of said vessel and encompassing a lower edge of said large cap.

4. The microwave heating digestion vessel of claim 1 wherein said spring assembly is made of fluorocarbons.

5. The microwave heating digestion vessel of claim 1 wherein said spring assembly is of a composite material.

6. The microwave heating digestion vessel of claim 1 wherein said spring assembly comprises a spring section having 1–10 turns.

7. The digestion vessel of claim 1 including number means on said small cap and a pointer affixed to said large cap for aligning said number means with said pointer for different pressure settings of said spring assembly.

8. The microwave heating system vessel of claim 1 wherein a spring protector sleeve extends over and about said spring assembly.

9. The microwave heating digestion vessel of claim 1 further comprises filter means positioned in a knurled nut which engages to said vent port is made of hydrophobic material.

10. The microwave heating digestion vessel of claim 1 including an exhaust tubing means connected from said vent port opening to a point external of said microwave heating cavity.

* * * * *